United States Patent
Jeon et al.

(10) Patent No.: US 9,345,807 B2
(45) Date of Patent: May 24, 2016

(54) PLGA SCAFFOLD

(71) Applicant: DAEGU GYEONGBUK INSTITUTE OF SCIENCE AND TECHNOLOGY, Daegu (KR)

(72) Inventors: Won Bae Jeon, Daegu (KR); Seong Kyoon Choi, Daegu (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 78 days.

(21) Appl. No.: 14/273,557

(22) Filed: May 9, 2014

(65) Prior Publication Data

US 2015/0030655 A1    Jan. 29, 2015

(30) Foreign Application Priority Data

May 10, 2013   (KR) .................. 10-2013-0053022

(51) Int. Cl.
*A61L 27/18* (2006.01)
*A61L 27/54* (2006.01)
*A61L 27/34* (2006.01)
*A61L 27/56* (2006.01)

(52) U.S. Cl.
CPC ............. *A61L 27/18* (2013.01); *A61L 27/34* (2013.01); *A61L 27/54* (2013.01); *A61L 27/56* (2013.01); *A61L 2300/21* (2013.01); *A61L 2300/428* (2013.01)

(58) Field of Classification Search
None
See application file for complete search history.

(56) References Cited

U.S. PATENT DOCUMENTS

| 6,391,049 B1 * | 5/2002 | McNally | A61B 17/00491 606/214 |
| 2004/0043135 A1 * | 3/2004 | Han | A61L 27/18 427/2.1 |

OTHER PUBLICATIONS

Jeon et al. "Functional enhancement of neuronal cell behaviors and differentiation by elastin-mimetic recombinant protein presenting Arg-Gly-Asp peptides" BMC Biotechnology Sep. 14, 2012, 12:61, pp. 1-9.*

Thomas Scientific "Falcon(c) Multiwell Plates for Cell Culture" accessed at http://www.thomassci.com/Laboratory-Supplies/Plates/_/BD-Falcon-Multiwell-Plates-For-Cell-Culture online on Sep. 18, 2015.*

* cited by examiner

*Primary Examiner* — Carlos Azpuru
*Assistant Examiner* — Casey Hagopian
(74) *Attorney, Agent, or Firm* — Gokalp Bayramoglu

(57) ABSTRACT

Disclosed is a PLGA (poly(D,L-lactide-co-glycolide)) cell scaffold. The cell scaffold is based on a PLGA scaffold, which is an FDA-approved material with no cytotoxicity, and overcomes the problem with conventional PLGA scaffolds of poor cell adhesion.

17 Claims, 12 Drawing Sheets

PLGA SCAFFOLD

TECHNICAL FIELD

The present invention relates to a PLGA (poly(D,L-lactide-co-glycolide)) cell scaffold. More particularly, the present invention relates to a cell scaffold which is based on a PLGA scaffold, an FDA-approved material with no cytotoxicity, but overcomes the problem with conventional PLGA scaffolds of poor cell adhesion.

BACKGROUND ART

In recent years, great progress has been made in the bioengineering field, particularly, tissue engineering for treating and regenerating tissues. Tissue engineering is an interdisciplinary field that applies the principles of cytology, life sciences, engineering and medical science toward the development of biological substitutes that restore, maintain or improve tissue function or a whole organ, based on the understanding of relationship between structures and functions of tissues. In other words, tissue engineering aims to maintain, enhance or restore functions of the body, using implantable, artificial bio-tissues. In this regard, tissue engineering is directed to the study of stem cell proliferation and differentiation, the decelopment of cyto- or biocompatible three-dimensional scaffolds, and the development of various tissue engineering tools. Of them, the three-dimensional scaffold for supporting stem cells or histocytes is an essential element in developing artificial tissues and organs.

Major requirements of scaffold materials for use in tissue regeneration are as follows. First, they should play a fully sufficient role as a substrate or frame where histocytes of interest are allowed to well adhere thereto and driven to form a tissue of desired three-dimension. Also, they should function as an intermediate barrier between implant cells and host cells. Accordingly, scaffold materials should be non-toxic and bio-compatible sufficiently not to incur blood coagulation or inflammation after transplantation. Another factor is biodegradability. Scaffold materials should be completely degraded in vivo with time after the implanted cells have been guided to perform full functions and roles as tissues. Hence, a scaffold is three-dimensionally fabricated mostly of a synthetic or natural polymer, or a composite thereof, with various morphologies and properties given thereto. Predominant among the currently commercial available synthetic biodegradable polymers are polyglycolic acid (PGA), polylactic acid (PLA), polylactic acid-glycolic acid copolymer (PLGA), poly-ε-caprolactone (PCL), and derivatives and copolymers thereof. Examples of natural biodegradable polymers used as scaffold materials include collagen, alginate, hyaluronic acid, gelatin, chitosan, and fibrin. The scaffold may be in various forms, such as sponges, gels, fibers, and microbeads, with the predominance of porous sponges and injectable hydrogel.

There are various technical problems with tissue engineering. Inter alia, the most urgent core technique in relation to scaffolds is to construct a cytocompatible surface environment. In light of the scaffol's intrinsic role of providing a three-dimensional environment advantageous for cell adhesion and growth, properties of scaffold's surface on which cell adhesion is made may be a decisive factor of current and future behaviors of the cells.

However, deficient basis studies on the use of cell scaffolds leads to the underdevelopment of cell scaffolds in human tissue-mimic three-dimensional structures, which, in turn, renders the application of cell scaffolds difficult.

DISCLOSURE

Technical Problem

Accordingly, the present invention has been made keeping in mind the above problems occurring in the prior art, and an object of the present invention is to provide a human body-mimic, three-dimensional, porous cell scaffold which is free of cytotoxicity and thus safe to the body, and has excellent biocompatibility, and a method for fabricating the same.

Technical Solution

The present invention provides a method for fabricating a cell scaffold, comprising: dissolving a PLGA (poly(D,L-lactide-co-glycolide)) substrate in an organic solvent to give a PLGA solution; and adding an effervescent agent to the PLGA solution to afford a PLGA scaffold with a porous structure.

In accordance with a preferred embodiment of the present invention, the method may further comprise coating the PLGA scaffold with an elastin-like artificial extracellular matrix.

In another preferred embodiment of the present invention, the elastin-like artificial extracellular matrix may be applied in an amount of 1 to 200 µg per 1 $cm^2$ of a cross sectional area of the PLGA scaffold.

In another preferred embodiment of the present invention, the method may further comprise treating the elastin-like artificial extracellular matrix-coated scaffold with a cytodifferentiation agent.

In another preferred embodiment of the present invention, the cytodifferentiation agent may comprise retinoic acid.

In another preferred embodiment of the present invention, the elastin-like artificial extracellular matrix may comprise a compound represented by the following General Formula 1:

  [General Formula 1]

(wherein, n is an integer meeting 2≤n≤10, and m is an integer meeting 10≤m≤30)

In another preferred embodiment of the present invention, the organic solvent comprises at least one selected from the group consisting of tetrahydrofuran, dimethyacetamide, dimethylformamide, chloroform, dimethylsulfoxide, butanol, isopropanol, isobutylalcohol, tetrabutylalcohol, acetic acid, 1,4-dioxane, toluene, ortho-xylene, and dichloromethane.

In another preferred embodiment of the present invention, the PLGA solution may contain the organic solvent in an amount of 4,000~5,000 weight parts based on 100 weight parts of PLGA.

In another preferred embodiment of the present invention, the PLGA solution may further comprise an organic acid.

In another preferred embodiment of the present invention, the organic acid may comprise citric acid.

In another preferred embodiment of the present invention, the PLGA solution may comprise the effervescent agent in an amount of 100~300 weight parts, and the organic acid in an amount of 2~20 weight parts, based on 100 weight parts of PLGA.

In another preferred embodiment of the present invention, the effervescent agent may comprise at least one selected from the group consisting of $NaHCO_3$, $Na_2CO_3$, $KHCO_3$, $K_2CO_3$, $CaCO_3$, and $Li_2CO_3$.

Also, the present invention provides a cell scaffold, comprising a PLGA (poly(D,L-lactide-co-glycolide) scaffold; and an elastin-like artificial extracellular matrix.

In one preferred embodiment of the present invention, the PLGA may contain a glycolide content of 80~150 weight parts per 100 weight parts of lactide.

In another preferred embodiment of the present invention, the PLGA scaffold may be coated with the elastin-like artificial extracellular matrix in an amount of 1 to 200 μg per cm$^2$ of a cross sectional area of the PLGA scaffold.

In another preferred embodiment of the present invention, the PLGA may have a molecular weight of 40,000~75,000.

In another preferred embodiment of the present invention, the elastin-like artificial extracellular matrix may comprise a compound represented by General Formula 1.

In another preferred embodiment of the present invention, the cell scaffold may further comprise a cytodifferentiation agent, In another preferred embodiment of the present invention, the cytodifferentiation agent may comprise retinoic acid.

In another preferred embodiment of the present invention, the PLGA scaffold may have a porous structure, with a porosity of 30~50%, as measured by image analysis of H&E-stained cross-sectional specimens.

Advantageous Effects

Exhibiting excellent biocompatibility with an improvement in cell adhesion and cell growth, the three-dimensional porous cell scaffold of the present invention can be applied to human bodies.

Prior to the elucidation of the present invention, terms used herein are defined as follows.

As used herein, the term "extracellular matrix (ECM)" refers to an intercellular part having a network structure composed mainly of proteins and polysaccharides.

As used herein, the term "artificial extracellular matrix" refers to an extracellular matrix, which plays an important role in cell attachment, migration and differentiation, artificially prepared by means of, for example, gene cloning, and is intended to encompass an artificial protein containing the arginyl glycyl aspartic acid (Arg-Gly-Asp (RGD)) motif involved in integrin mediated interaction, with an elastin mimetic protein serving as a backbone.

MODE FOR INVENTION

A better understanding of the present invention may be obtained through the following examples which are set forth to illustrate, but are not to be construed as limiting the present invention.

Below, a detailed description will be given of the present invention.

As mentioned above, deficient basis studies on the use of cell scaffolds leads to the underdevelopment of cell scaffolds in human tissue-mimic three-dimensional structures, which, in turn, renders the application of cell scaffolds difficult.

In order to overcome the aforementioned problems, the present invention provides a three-dimensional porous cell scaffold comprising a PLGA (Poly(D,L-lactide-co-glycolide)) substrate, and an elastin-like artificial extracellular matrix, which is so highly biocompatible as to guarantee an improvement in cell adhesion and proliferation, thus offering various applications to human bodies.

Fabricated from an elastin-like artificial extracellular matrix plus a PLGA scaffold, the cell scaffold of the present invention is advantageous in terms of cell adhesion and cell proliferation over conventional PLGA scaffolds.

So long as its morphology and material is typically acceptable, any PLGA scaffold may be used in the present invention without limitations. Preferably, it may range in molecular weight from 40,000 to 75,000, with 80~150 weight parts of glycolide per 100 weight parts of lactide.

Also, any size of the PLGA scaffold may be taken without limitations if it is available for typical cell scaffolds. The PLGA scaffold may be tailored to suitable size and morphology depending on the site where tissue regeneration is intended. Its dimensions may be preferably on the order of 3 cm×5 cm×3 cm~10 cm×15 cm×10 cm ((length×width× height), and more preferably on the order of 5 cm×7 cm×5 cm~7 cm×10 cm×7 cm (length×width×height), but is not limited thereto.

Further, no particular limitations are imposed on the structure of the PLGA scaffold if it is available for typical cell scaffold. Preferably, the PLGA may be porous, and more preferably may have a porosity of 30~50%, as measured by image analysis of H&E-stained cross-sectional specimens.

Figure 10:
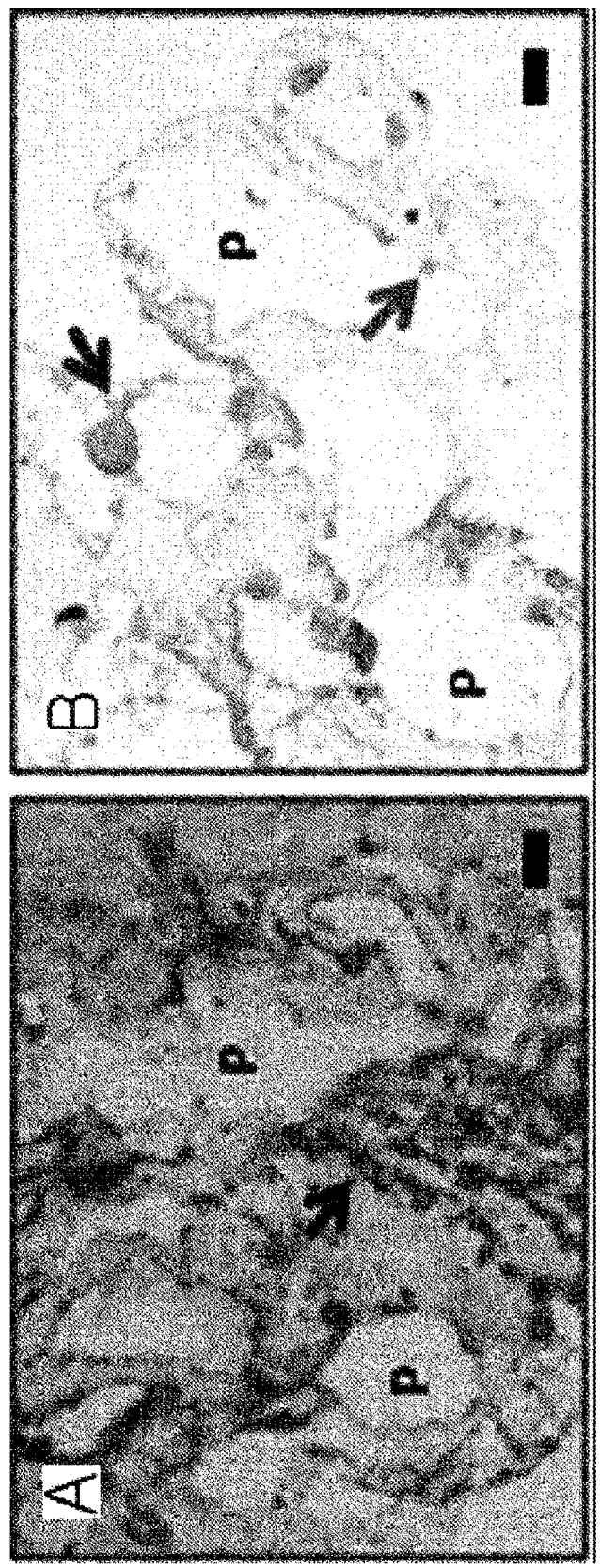
FIG. 10 is an image J of H&E-stained cross-sectional specimens from SS, taken in the manner described in Test Example 2-2 (A: small droplet of the REP applied to the PLGA scaffold, B: big droplet of the REP applied to the PLGA scaffold).
Figure 11:
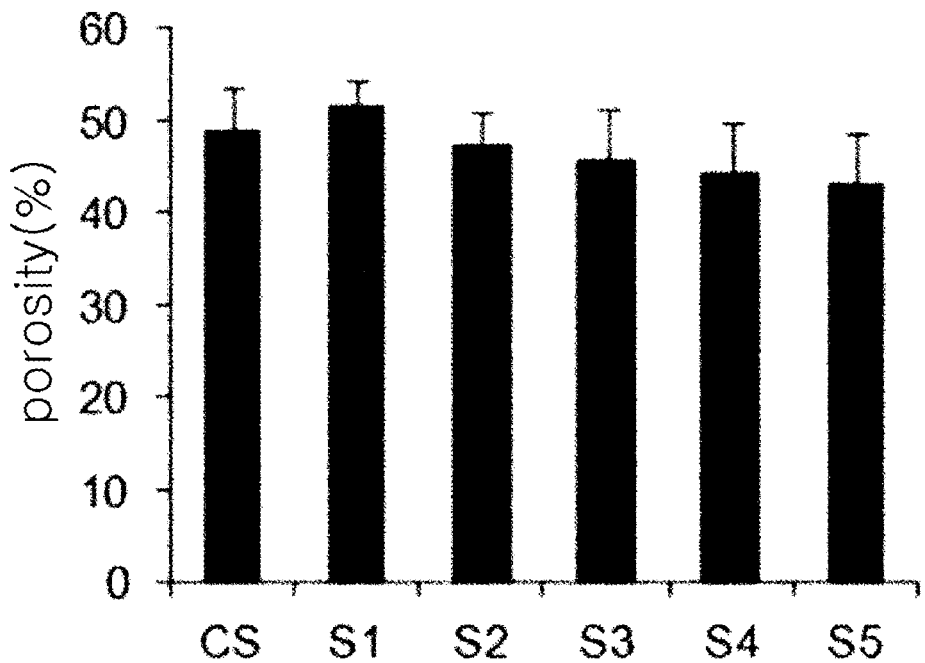
FIG. 11 is a graph showing the porosity of the scaffolds, as measured in Test Example 2-2.

As illustrated in Test Example 2 and FIGS. 10 and 11, the PLGA scaffold of the present invention has a porous structure with a porosity of 40~50%.

Turning to the elastin-like artificial extracellular matrix, it is applied to the PLGA scaffold and configured to enhance both the cell adhesion and the cell growth which are poor with conventional PLGA alone. Any elastin-like artificial extracellular matrix that is prepared using a typical method or that is commercially available may be used in the present invention. Preferably, the elastin-like artificial extracellular matrix may contain a compound represented by the following General Formula 1, and more preferably, the compound of TGPG[VGRGD(VGVPG)$_6$]$_{20}$WPC(REP).

    [General Formula 1]

(wherein, n is an integer meeting 2≤n≤10, and m is an integer meeting 10≤m≤30)

In addition, when the elastin-like artificial extracellular matrix is applied to the PLGA scaffold, its amount is not particularly limited. Preferably, the PLGA scaffold may be coated with the elastin-like artificial extracellular matrix in an amount of 1 to 200 μg, and more preferably in an amount of 3 to 150 μg, per cm² of the cross sectional area of the PLGA scaffold.

For example, when the amount of the elastin-like artificial extracellular matrix applied to the PLGA scaffold exceeds 200 μg per 1 cm² of the cross sectional area of the PLGA scaffold, the porous structure of the PLGA scaffold surface may be blocked. On the other hand, when the applied amount of the elastin-like artificial extracellular matrix is below 1 μg per 1 cm² of the cross sectional area of the PLGA scaffold, the PLGA scaffold becomes too poor in biocompatibility to be used in a cell scaffold.

In one embodiment of the present invention, the cell scaffold may further comprise a cytodifferentiation agent.

Any cytodifferentiation agent that is typically available for differentiating cells may be used in the present invention, without limitations. Preferable, however, is retinoic acid.

No particular limitations are imposed on the concentration of the cytodifferentiation agent in the cell scaffold. However, the concentration may be preferably on the order of 1~20 μM and more preferably on the order of 5~13 μM.

Also, the present invention addresses a method for fabricating a cell scaffold, comprising dissolving a PLGA (poly(D,L-lactide-co-glycolide)) substrate in an organic solvent to give a PLGA solution; and adding an effervescent agent to the PLGA solution to afford a PLGA scaffold.

First, a PLGA solution is obtained by dissolving a PLGA (poly(D,L-lactide-co-glycolide)) substrate in an organic solvent.

Any PLGA scaffold thus is prepared using a typical method or that is commercially available may be used in the present invention. Preferably, the PLGA scaffold has a molecular weight of 40,000~75,000, with a glycolide content of 80~150 weight parts per 100 weight parts of lactide.

The concentration of the PLGA solution is not particularly limited. However, the PLGA solution may preferably comprises an organic solvent in an amount of 4,000~5,000 weight parts, and more preferably in an amount of 4,200~4,500, based on 100 weight parts of PLGA.

No particular limitations are imposed on the organic solvent if it is typically used for dissolving PLGA. Preferably, it may be selected from the group consisting of tetrahydrofuran, dimethylacetamide, dimethylformamide, chloroform, dimethylsulfoxide, butanol, isopropanol, isobutylalcohol, tetrabutylalcohol, acetic acid, 1,4-dioxane, toluene, ortho-xylene, dichloromethane, and a combination thereof.

Next described is the step in which the PLGA scaffold in a porous structure is obtained by adding an effervescent agent to the PLGA solution.

So long as it allows for the preparation of a porous PLGA scaffold from a PLGA solution and an effervescent agent, any process may be available for the present invention. Preferably, a gas foaming method using PLGA and an effervescent agent may be applied to the preparation of a porous PLGA scaffold.

If the effervescent agent is typically available for the fabrication of a porous structure of a cell scaffold, no particular limitations are imposed thereon. Preferably, the effervescent agent may comprise at least one selected from the group consisting of NaHCO$_3$, Na$_2$CO$_3$. KHCO$_3$, K$_2$CO$_3$, CaCO$_3$ and Li$_2$CO$_3$.

Further, the amount of the effervescent agent added to the PLGA solution is not limited, but may be preferably on the order of 1,000~2,000 weight parts based on 100 weight parts of PLGA.

In one embodiment of the present invention, the PLGA solution may comprise an effervescent agent and an organic acid.

If the organic acid is typically available for cell scaffolds, no particular limitations are imposed thereon. However, preferable is citric acid.

Amounts of the effervescent and the organic acid in the PLGA solution are not particularly limited. The PLGA solution may preferably comprise an effervescent in an amount of weight parts and an organic acid in an amount of 2~20 weight parts, based on 100 weight parts of PLGA, and more preferably an effervescent in an amount of 150~230 weight parts and an organic acid in an amount of 5~15 weight parts.

Also, any size of the PLGA scaffold may be taken without limitations if it is available for typical cell scaffolds. The PLGA scaffold may be tailored to suitable size and morphology depending on the site where tissue regeneration is intended. Its dimensions may be preferably on the order of 3 cm×5 cm×3 cm~10 cm×15 cm×10 cm ((length×width×height), and more preferably on the order of 5 cm×7 cm×5 cm 7 cm×10 cm×7 cm (length×width×height), but is not limited thereto.

In one embodiment of the present invention, the method may further comprise applying an elastin-like artificial extracellular matrix to a surface of the PLGA scaffold.

Configured to enhance both the cell adhesion and the cell growth which are poor with conventional PLGA alone, the elastin-like artificial extracellular matrix is applied to the PLGA scaffold. Any elastin-like artificial extracellular matrix that is prepared using a typical method or that is commercially available may be used in the present invention. Preferably, the elastin-like artificial extracellular matrix may contain a compound represented by the following General Formula 1:

    [General Formula 1]

(wherein, n is an integer meeting 2≤n≤10, and m is an integer meeting 10≤m≤30).

In addition, no particular limitations are imposed on the amount of the elastin-like artificial extracellular matrix that is applied to the PLGA scaffold.

Preferably, the PLGA scaffold may be coated with the elastin-like artificial extracellular matrix in an amount of 1 to 200 μg, and more preferably in an amount of 3 to 150 μg, per cm$^2$ of the cross sectional area of the PLGA scaffold.

For example, when the amount of the elastin-like artificial extracellular matrix applied to the PLGA scaffold exceeds 200 μg per 1 cm$^2$ of the cross sectional area of the PLGA scaffold, the porous structure of the PLGA scaffold surface may be blocked. On the other hand, when the applied amount of the elastin-like artificial extracellular matrix is below 1 μg per 1 cm$^2$ of the cross sectional area of the PLGA scaffold, the PLGA scaffold becomes too poor in biocompatibility to be used in a cell scaffold.

In one embodiment of the present invention, the method may further comprise treating the elastin-like artificial extracellular matrix-coated cell scaffold with a cytodifferentiation agent.

Any cytodifferentiation agent that is typically available for differentiating cells may be used in the present invention, without limitations. Preferable, however, is retinoic acid.

No particular limitations are imposed on the concentration of the cytodifferentiation agent in the cell scaffold. However, the concentration may be preferably on the order of 1~20 μM and more preferably on the order of 5~13 μM.

EXAMPLES

Example 1

Preparation of Elastin-Like Artificial Extracellular Matrix

The TGPG[VGRGD(VGVPG)$_6$]$_{20}$WPC (REP) matrix was used as an elastin-like artificial extracellular matrix. The REP matrix was obtained using the plasmid pET-25b(+)-1 (Novagen, U.S.A.). After being expressed, the REP matrix was isolated from *E. coli* BLR(DE3) by inverse thermal cycling. Then, the REP matrix was dissolved in PBS (phosphate buffered saline; pH 7.4, Gibco, U.S.A.).

Example 2

Fabrication of Cell Scaffold

A cell scaffold was fabricated on the basis of PLGA (poly (D,L-lactide-co-glycolide), lactide:glycolide=50:50, Mw 40,000-75,000, Sigma-Aldrich, U.S.A.). In this context, the PLGA scaffold was prepared by a gas foaming method using NaHCO$_3$ (Duksan Chemicals, Korea) as an inducer. In a falcon tube, 1 g of PLGA was dissolved in 30 ml of CHCl$_3$ with the aid of a shaking rotator. This PLGA solution was aliquoted to 10 vials (width 1.5 cm×height 6.5 cm), each containing 2 g of NaHCO$_3$ (diameter 53~106 μm), with the mass ratio of NaHCO$_3$:PLGA set forth as 15:1. Afterwards, the PLGA solution was dried for 2 days under a laminar flow hood and then, for 12 hrs at 25° C. in a vacuum to give a PLGA scaffold. This PLGA scaffold was rendered porous by treatment with 5 ml of citric acid in the vial for 2 days on a shaking rotator. After removal of the citric acid from the vial by aspiration, the PLGA scaffold was washed twice with 5 ml of PBS, and dried at 25° C. for 12 hrs in a vacuum to afford a porous PLGA scaffold.

Example 3

Surface Modification of PLGA Scaffold

Figure 1:
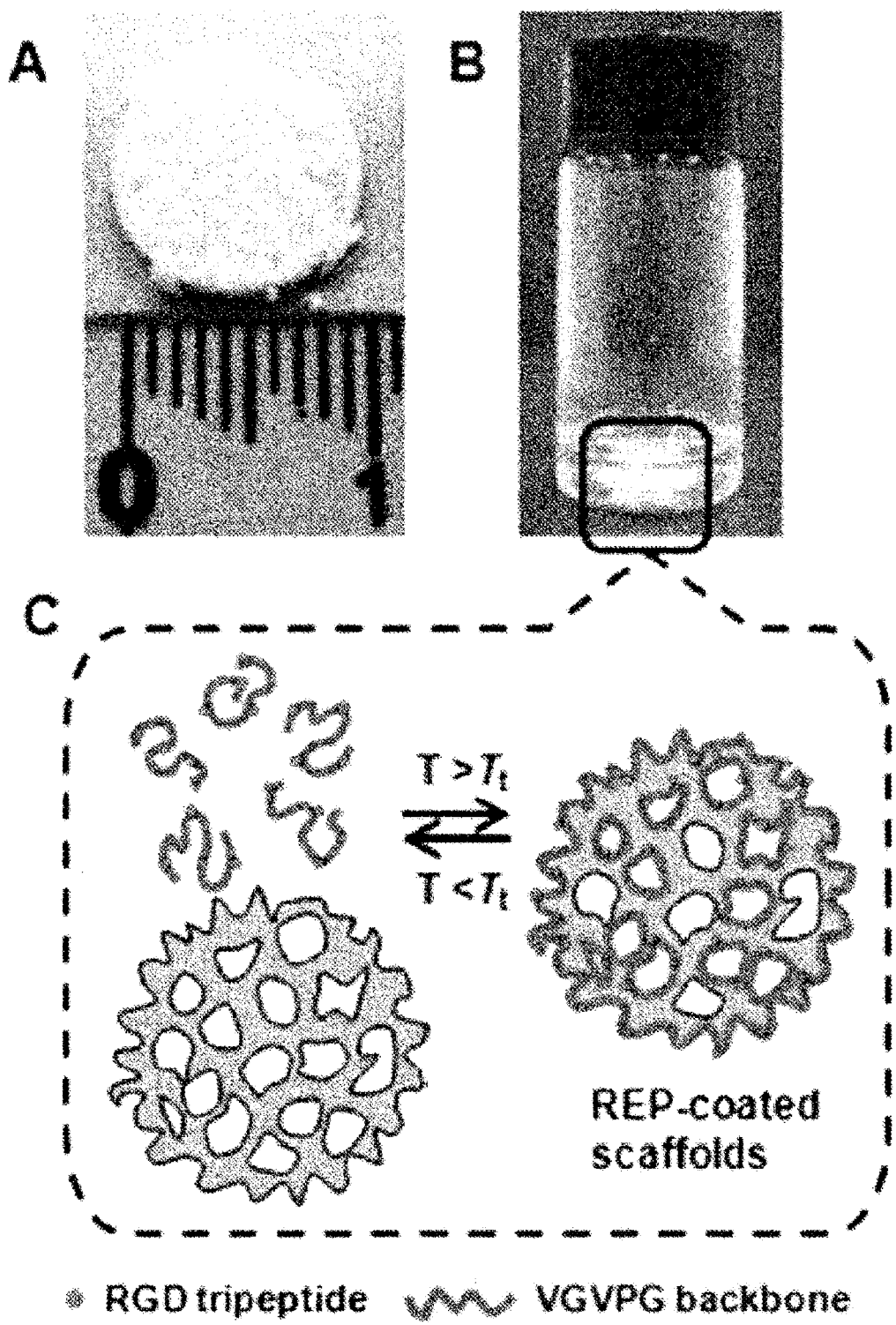
FIG. 1 is a schematic view illustrating the process of coating the surface of a PLGA scaffold with an REP matrix.

The PLGA scaffold prepared in Example 2 was immersed, together with 30 μg, 60 μg, 300 μg, 600 μg or 1200 μg of the REP matrix prepared in Example 1, in 1 ml of PBS in a vial (diameter 2 cm×5 cm) and left for 2 hrs at 4° C. Then, the PLGA scaffold was incubated at 37° C. for 1 hr in a cell culture chamber to allow for surface modification thereon. The procedure of coating the PLGA scaffold with the REP matrix is illustrated in FIG. 1.

FIG. 1A is a macroscopic appearance of the PLGA scaffold while FIG. 1B shows the PLGA scaffold immersed in the REP matrix. FIG. 1C schematically illustrates the process of modifying the surface of the PLGA scaffold with the REP matrix through thermal transformation.

Hereinafter, the PLGA scaffold was designated S1 when coated with 30 μg of the REP matrix, S2 when coated with 60 μg of the REP matrix, S3 when coated with 300 g of the REP matrix, S4 when coated with 600 μg of the REP matrix, and S5 when coated with 1,200 gig of the REP matrix.

Test Example 1

FT-IR Spectrum

The REP-coated PLGA scaffolds prepared in Example 3 were analyzed for chemical structure by FT-IR spectrometry (Nicolet FT-IR 380) at wavelengths of 4000~525 cm. The FT-IR spectra were analyzed using the OMNIC™ software, and are shown in FIG. 2.

Figure 2:
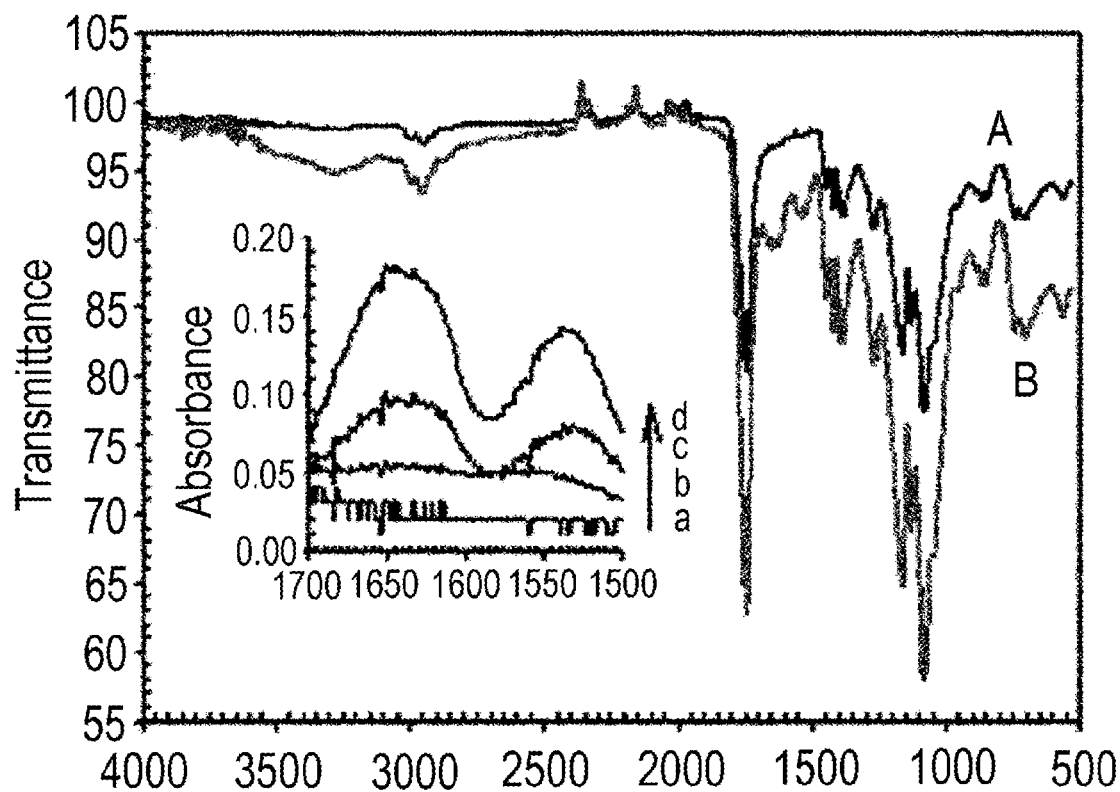
FIG. 2 shows FT-IR spectra of the PLGA scaffolds (A: PLGA scaffold (CS) prepared in Example 2, B: PLGA scaffold (S3) prepared in Example 3).

As can be seen in FIG. 2, the spectra of the PLGA scaffold (CS) prepared in Example 2 had peaks at 3000-2800 cm$^{-1}$ for a C—H bond, at 1750-1735 cm$^{-1}$ for a C=O bond, at 1470-1430 cm$^{-1}$ for a CH$_3$ asymmetric bond, at 1425 cm$^{-1}$ for a CH$_2$—C=O asymmetric bond, at 1395-1365 cm$^{-1}$ for a CH$_3$ symmetric bond, at 1330-1050 cm$^{-1}$ for C=O and O—C—C bonds, at 1250-800 cm$^{-1}$ for a CH$_3$ bond, and at 770-720 cm$^{-1}$ for a CH$_2$ bond.

In addition, FIG. 2 shows the appearance of three new signature peaks (3288 cm$^{-1}$, 1645 cm$^{-1}$ and 1539 cm$^{-1}$) on the spectrum of the PLGA scaffold coated with 300 μg of the REP matrix (S3) prepared in Example 3. These peaks accounted for amides A, I and II on the extracellular matrix (polypeptide), respectively. The amide A peak was attributed to the peptide N—H bond coupled with hydrogen bond while the amide I peak was derived from the N—H bond vibration coupled with the C=O bond, and the amide II peak from the C—N bond vibration coupled with the N—H bond.

None of the peaks of amides A, I and II were detected from the PLGA scaffold of Example 2, which was not coated with the REP matrix, indicating that the PLGA scaffold could be coated with the REP matrix even without a chemical reaction induced therebetween.

Also as is apparent from data of FIG. 2, the integration region of the amide II bond was observed to amplify by four and ten folds with an increase of the concentration of REP matrix from 30 μg/ml to 120 μg/ml and to 300 μg/ml, respectively.

Test Example 2

Properties of PLGA Scaffold

Test Example 2-1

SEM

Figure 3:
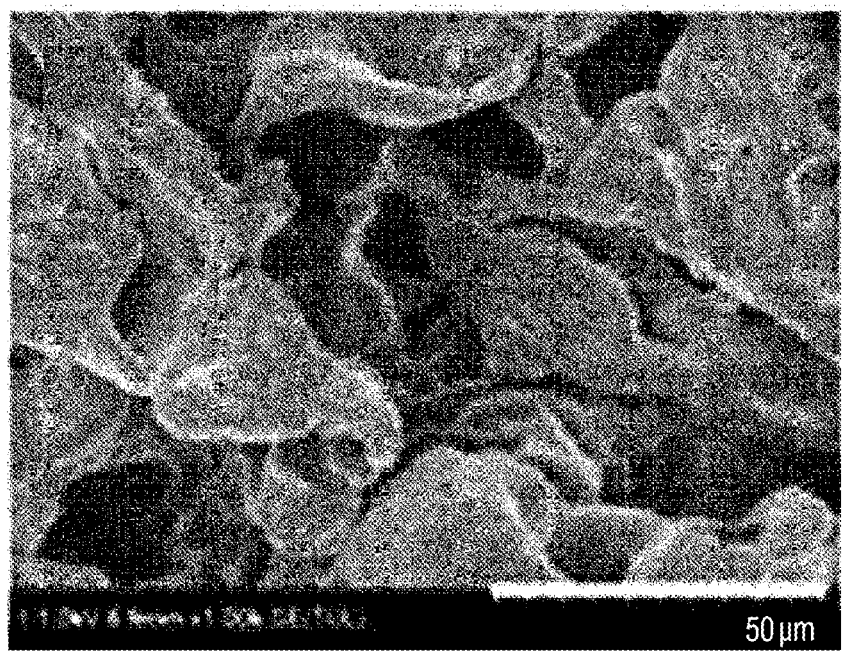
FIG. 3 is an SEM image of the PLGA scaffold (CS) prepared in Example 2, taken in the manner described in Test Example 2-1.
Figure 4:
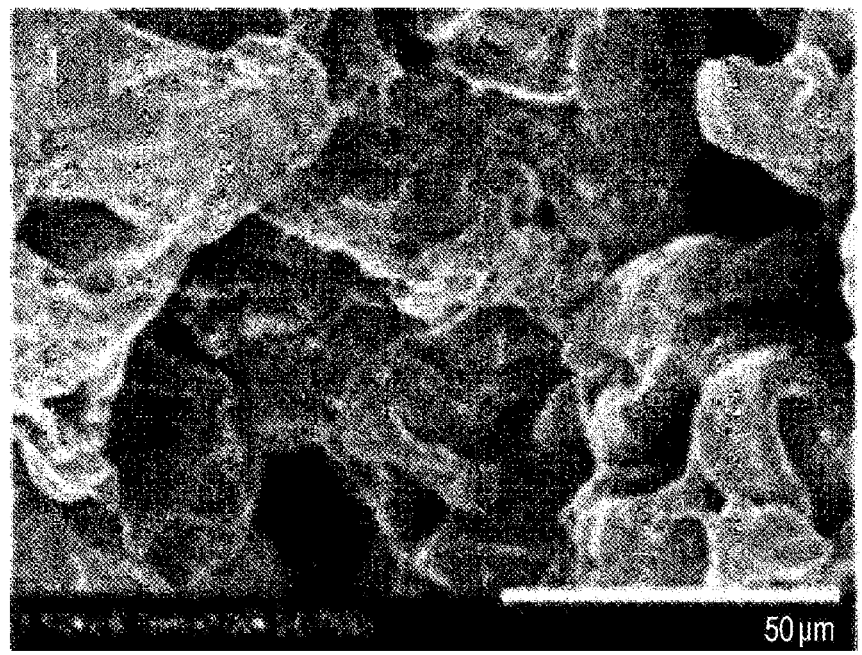
FIG. 4 is an SEM image of the REP matrix-coated PLGA scaffold (S1) prepared in Example 3, taken in the manner described in Test Example 2-1.
Figure 5:
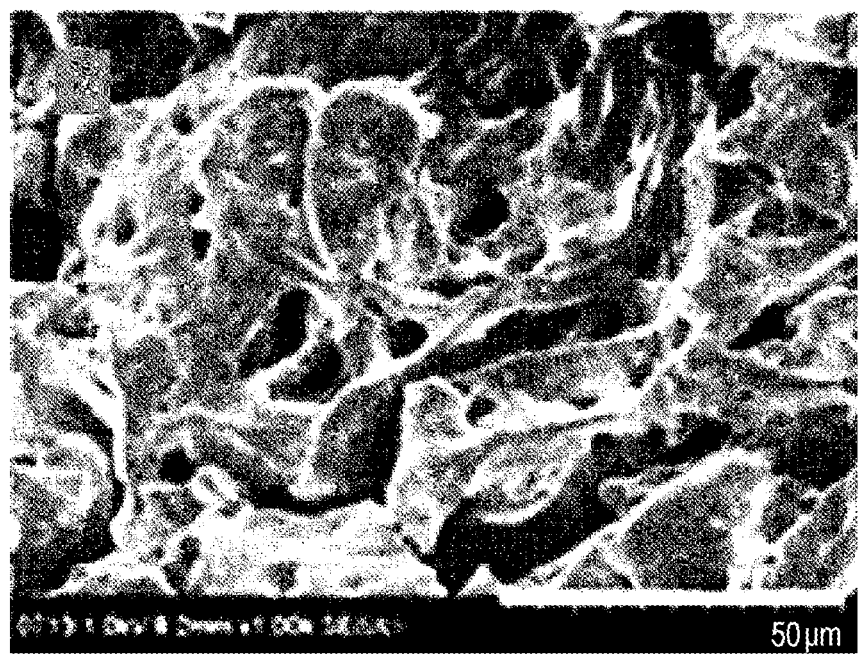
FIG. 5 is an SEM image of the REP matrix-coated PLGA scaffold (S2) prepared in Example 3, taken in the manner described in Test Example 2-1.
Figure 6:
FIG. 6 is an SEM image of the REP matrix-coated PLGA scaffold (S3) prepared in Example 3, taken in the manner described in Test Example 2-1.
Figure 7:
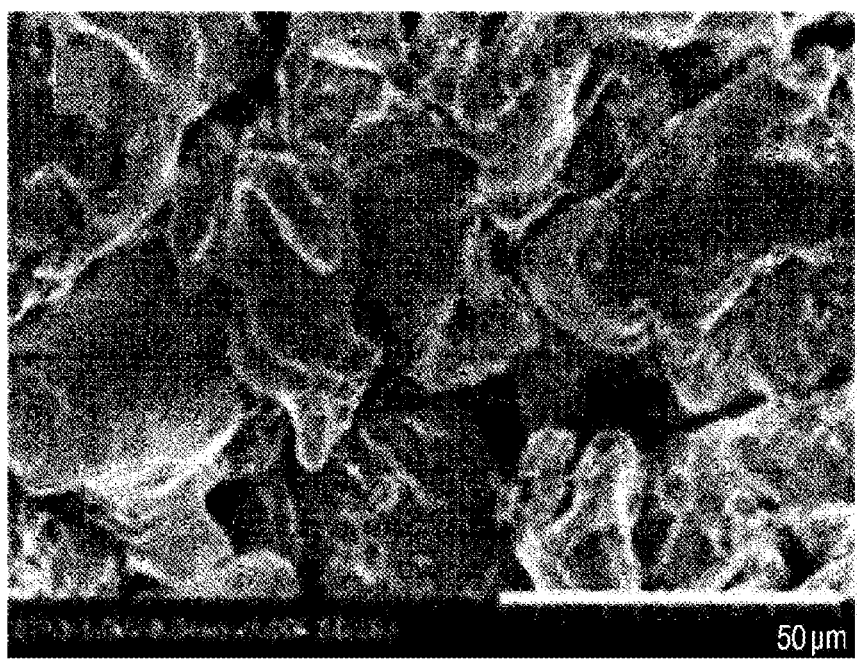
FIG. 7 is an SEM image of the REP matrix-coated PLGA scaffold (S4) prepared in Example 3, taken in the manner described in Test Example 2-1.

The PLGA scaffold and the REP matrix-coated PLGA scaffold, respectively prepared in Examples 2 and 3, were photographed using Hitachi 4800 Scanning Electron Microscope (SEM). The SEM images are shown for the PLGA scaffold (CS) prepared in Example 2 in FIG. 3, and the REP matrix-coated PLGA scaffolds prepared in Example 3 in FIGS. 4 (S1), 5 (S2), 6 (S3), 7 (S4), and 8 (S5).

Figure 8:
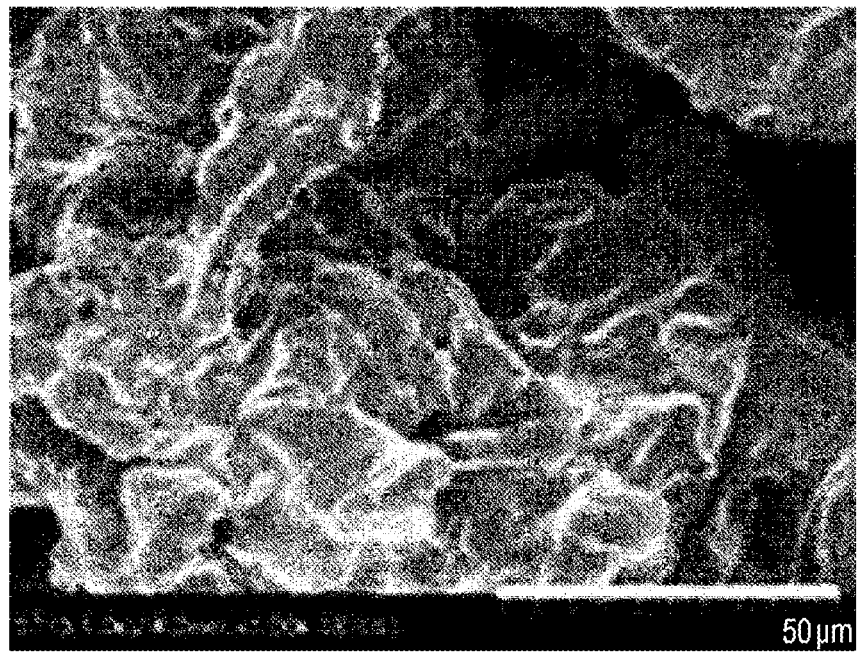
FIG. 8 is an SEM image of the REP matrix-coated PLGA scaffold (S5) prepared in Example 3, taken in the manner described in Test Example 2-1.

As can be seen in FIGS. 3 to 7, smooth surface properties were visualized in the SEM images of CS, S1, S2, S3 and S4 while the SEM image of FIG. 8 displayed a wrinkled surface with a size of 15 μm or less.

Test Example 2-2

Porosity Measurement

The PLGA scaffold (CS) of Example 2 and the REP matrix-coated PLGA scaffolds (S1~S5) of Example 3 were measured for porosity parameters at 25° C. under 1 atm, and porosity was calculated from the measurements according to the following Mathematical Formula I:

$$\text{Porosity} = \left(1 - \frac{D_{scaffold}}{D_{material}}\right) \times 100 \quad \text{Math Formula 1}$$

wherein $D_{scaffold}$ is a density of the scaffold as represented by a ratio of scaffold mass/scaffold volume, and $D_{material}$ is a density of the material used for the fabrication of the scaffold. For this, the PLGA and the REP matrix had a density of 1.25 g/cm³ and 1.22 g/cm³.

In addition, porosity was measured from H&E-stained cross-sectional specimens using Image J, and the result is given in FIG. 11.

Pore sizes and pore structures were also evaluated from Image J of H&E-stained cross-sectional specimens. Image J results of pore sizes and pore structures are given in FIG. 9 for CS and in FIG. 10 for S4.

In FIGS. 10A and 10B, a pink or violet portion represents a REP matrix layer, with small water drop-like morphologies apparently observed on the surface or border of the scaffold. The small water drop-like morphologies measured 5~50 μm in diameter.

Figure 9:
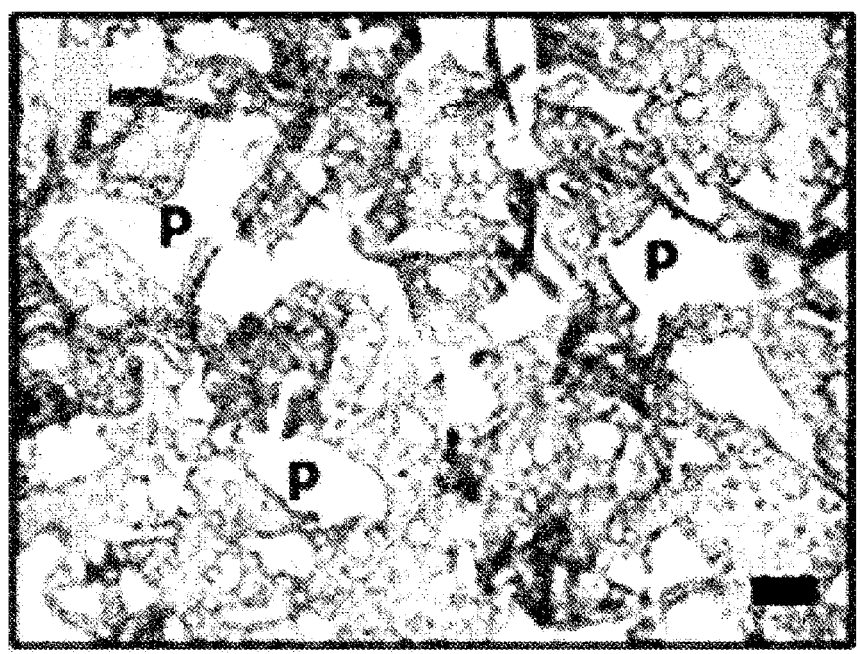
FIG. 9 is an image J of an H&E-stained cross-sectional specimen from CS, taken in the manner described in Test Example 2-2.

There were desired links between pores, as visualized in the SEM images of FIGS. 3 to 8 and the H&E images of FIGS. 9 and 10.

As illustrated in FIG. 11, the porosity was measured to be 48.8% for CS, 51.3% for S1, 47.3% for S2, 45.5% for S3, 44.2% for S4, and 42.9% for S5, indicating that the porosity of the PLGA scaffold decreased with an increase in the concentration of the REP matrix applied to the PLGA scaffold.

Test Example 3

Assay for Cell Adhesion and Proliferation

Test Example 3-1

Cell Adhesion Assay

Figure 12:
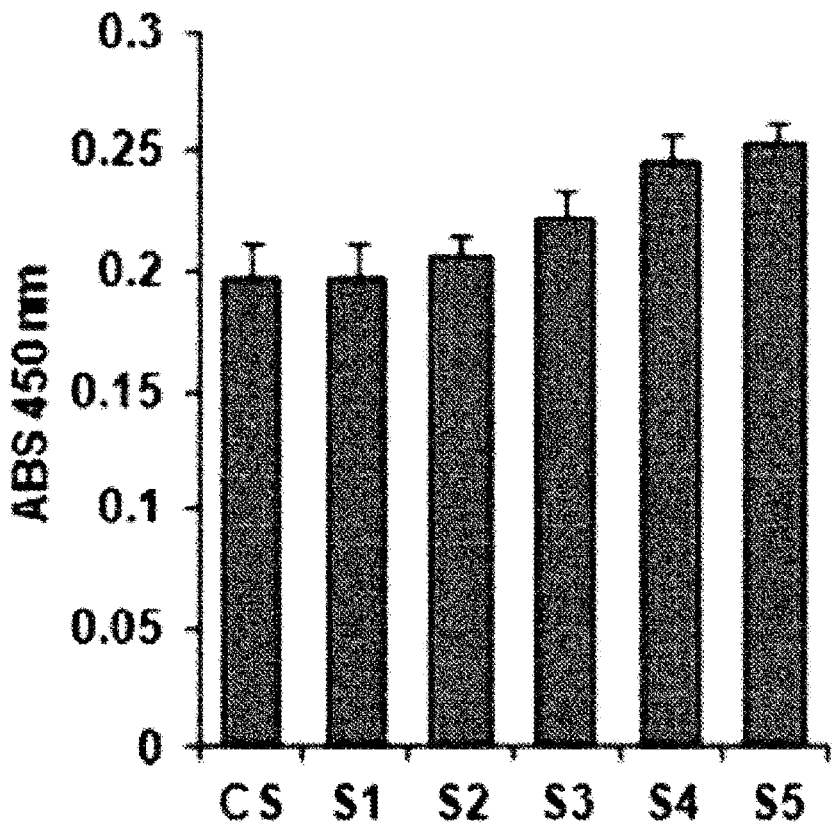
FIG. 12 is a graph showing the absorbance of cells grown on the scaffolds, as measured by the cell adsorption assay of Test Example 3-1.

For a cell adhesion assay, the PLGA scaffold (CS) of Example 2 and the REP matrix-coated PLGA scaffolds (S1 to S5) of Example 3, each with dimensions of 6.5 mm (diameter)×2 mm (height), were plated into respective wells of 96-well plates. The PLGA scaffolds were prevented from floating by fixture the bottom of each well using O-ring. UV sterilization was performed overnight. Subsequently, NPCs ($5\times10^4$ cells in 100 μl of NCM) were seeded to the plates, and incubated for 8 hrs at 37° C. in a 5% $CO_2$ chamber. The scaffolds on which the cells grew were transferred to new 96-well plates. For counting cells of the new 96-well plates, 90 μl of Neural Cellutions Medium (NCM, DV Biologic, USA), together with 10 μl of CCK-8 (Cell Counting Kit-8, Dojindo, Japan), was added to each other before incubation for 1 hr at 37° C. Absorbance at 450 nm was read on the Multiskan Ex microplate reader. Absorbance measurements are shown in FIG. 12.

NPCs (PN003-F, DV Biologics, USA) were cultured in NCM supplemented with N-Gri-001-S (1%, DV Biologics, USA), N2 supplement (1%, DV Biologics, USA), 20 ng/ml fibroblast growth factor (Gibco), 20 ng/ml epidermal growth factor (Gibco), 1% penicillin/streptomycin (Gibco), and 2.5 μg/ml amphotericin B (Gibco). Subsequently, FBS was added in an amount of 10% to NCM for cell adhesion assay and in an amount of 1% to NCM for cell differentiation assay.

Test Example 3-2

Cell Proliferation Assay

Of two 24-well plates for use in cell proliferation assay, one was intended for 3-day growth (A) while the other was for 6-day growth (B). In the plates, the PLGA scaffold of Example 2 and the REP matrix-coated PLGA scaffolds (S1 to S5) of Example 3, each with dimensions of 6.5 mm (diameter)×2 mm (height), were plated into respective wells of 96-well plates. UV sterilization was performed overnight. Subsequently, NPCs ($1\times10^5$ cells in 500 μl of NCM) were seeded to the plates, and incubated at 37° C. in a 5% $CO_2$ chamber.

After 3 days of incubation, the plate (A) was withdrawn from the $CO_2$ chamber, and 50 μl of CCK-8 was added to each well before measuring absorbance at 450 nm. Absorbance measurements are shown in FIG. 13.

The other plate (B) was also withdrawn from the $CO_2$ chamber after 6 days of incubation, followed by adding 100 μl of CCK-8 to each well. Absorbance at 450 nm was measured and is shown in FIG. 13.

As can be seen in FIG. 12, the NPC adhesion rate was increased with an increase in the concentration of the REP matrix coated, as set forth to be 100% for S1, 105.5% for S2, 113.1% for S3, 125.0% for S4, and 129.8% for S5, relative to CS.

Figure 13:
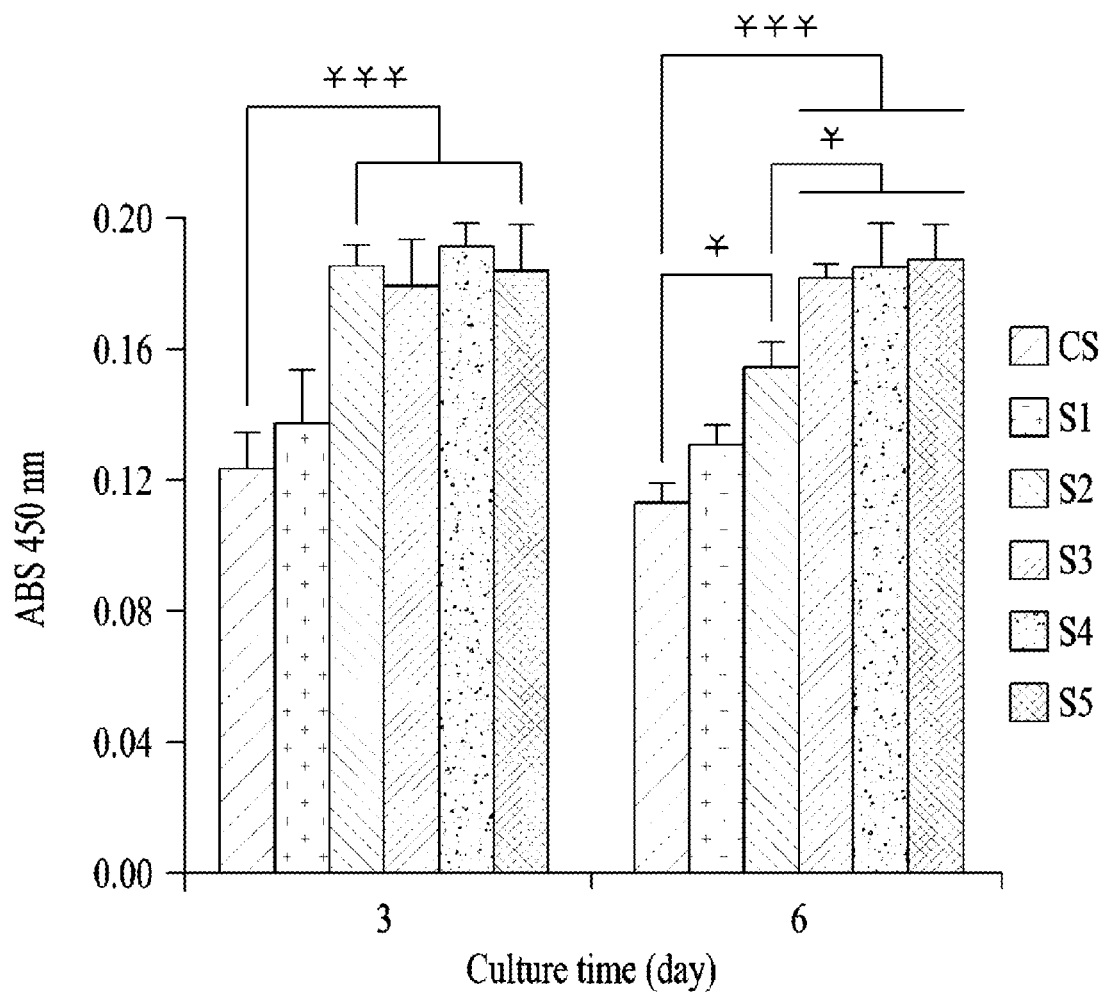
FIG. 13 is a graph showing the absorbance of cells grown on the scaffolds, as measured by the cell proliferation assay of Test Example 3-2.

From the data of FIG. 13 on NPC cell proliferation after three and six days of incubation, analysis was made of effects of the REP matrix coating on NPC cell growth. Compared to the control CS, the cells were allowed to outgrow by 116.2% in S1, by 150.6% in S2, by 146.1% in S3, by 155.3% in S4, and by 150.4% in S5 after 3 days incubation, and by 115.4% in S1, by 136.7% in S2, by 160.1% in S3, by 163.6% in S45, and by 165.4% in S5 after six days of incubation.

These data demonstrate that cells grow well on the REP-coated cell scaffold, compared to the non-coated cell scaffold, and the cell adhesion and proliferation is promoted as the REP concentration increases. Accordingly, the REP-coated PLGA cell scaffold is more suitable for use in cell growth than non-coated cell scaffolds.

Test Example 4

Cell Differentiation Assay

For a cell differentiation assay, NPCs were cultured for 24 hrs on the PLGA scaffold (CS) of Example 2 and the REP matrix-coated PLGA scaffolds (S1 to S5) of Example 3, each with dimensions of 10 mm (diameter)×2 mm (height), in the same manner as in Test Example 1. Cell differentiation was induced by 10 µM RA (all-trans-retinoic acid), and analyzed 4 or 8 days after induction.

Figure 14:
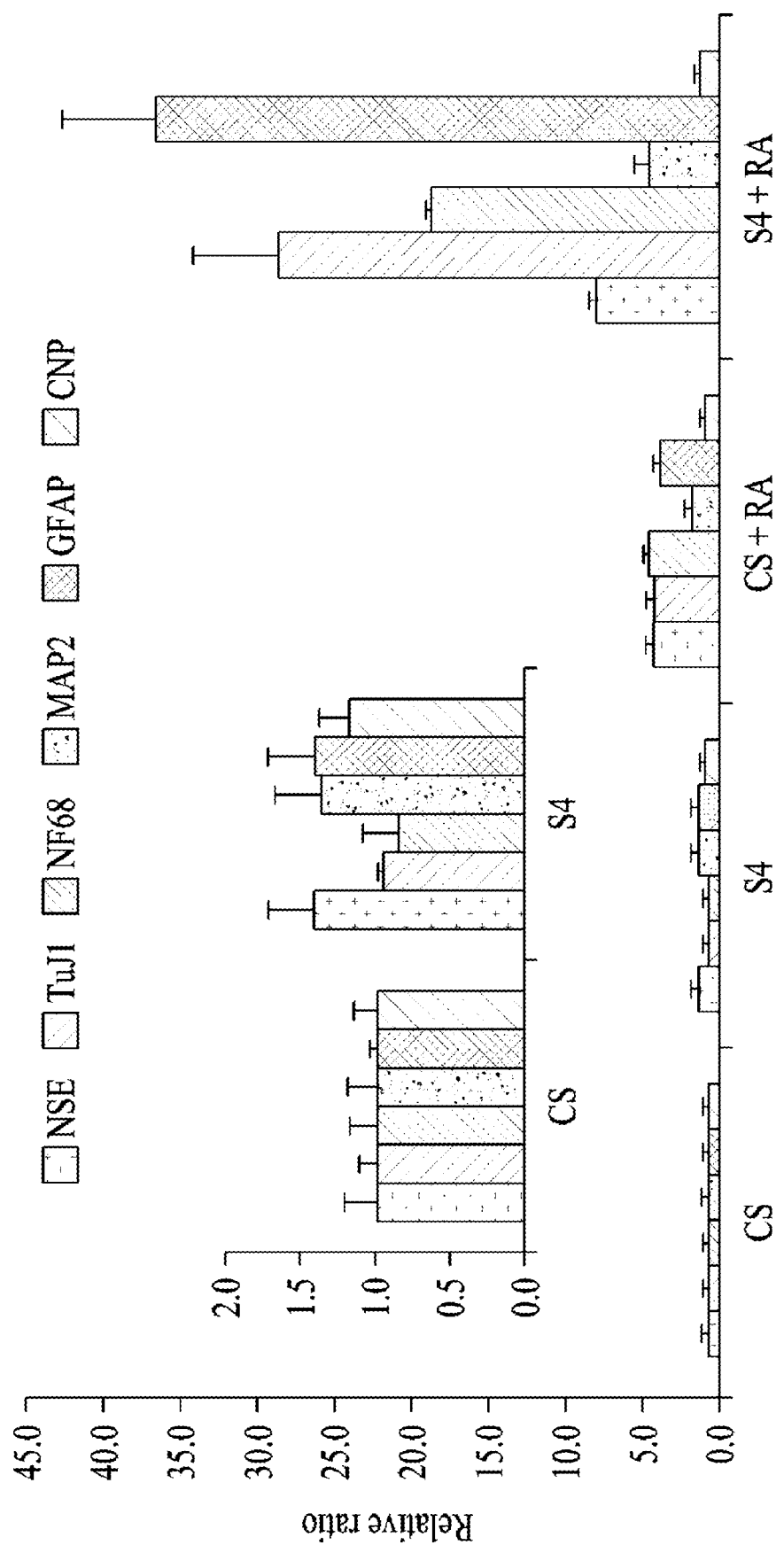
FIG. 14 is a graph showing degrees of cell differentiation, as analyzed by the qRT-PCR of Test Example 4.

The efficacy of the REP matrix coating in NPC differentiation was evaluated as relative abundance of 5 neuron biomarker mRNA transcripts (NSE, TuJ1, NF68, MAP2 for neurons, GFAP for astrocyte), and CNP for chondrocyte by qRT-PCR. qRT-PCR results are shown in FIG. 14.

qRT-PCR (Quantitative real-time PCR) analysis was done as follows. RNA used in experiments was isolated from the same NPCs as in Test Experiment 3, with the aid of an RNeasy kit (Qiagen, USA). From 4 µg of the RNA, cDNA was synthesized using a high-capacity cDNA reverse transcription kit (Applied Biosystems, USA). For qRT-PCR analysis, SYBR Green PCR master mix kit (Applied Biosystems, USA) was employed in ABI 7500 RT-PCR. In this regard, qRT-PCR started with heating for 2 min at 50° C. and then for 10 min at 95° C., an proceeded with 40 thermal cycles of 95° C. for 15 sec, and 60° C. for 1 min. Primer sets were designed on the basis of human gene sequence frameworks available from the GenBank using the primer express 3.0 software (Applied Biosystems. USA).

In the absence of retinoic acid (RA), as shown in FIG. 14, expression levels of NSE, MAP2, GFAP, and CNP in the S4 scaffold were similar to those in the REP coat-devoid PLGA scaffold CS, prepared in Example 2.

After treatment with RA, all of the markers, except for CNP, were expressed 1.8~6.9-fold more abundantly in terms of mRNA level than CS. In cells grown on S4 in the presence of RA, the relative abundance of mRNAs for the markers were measured in the following order: GFAP (36.7%), TuJ1 (28.8%), NF68 (19.1%/), NSE (8.0%), MAP2 (4.6%) and CNP (1.5%).

Moreover, combined treatment with REP and RA increased the expression of CNP by 1.4 folds in S4, compared to CS.

In addition, mRNAs of neural and astroglial markers expressed in cells grown in the presence of RA on S4 were higher than either those in the absence of RA on S4 or those in the presence of RA on CS.

TuJ1 NF68, NSE, and MAP2 are differentiation markers of neuronal cells while GFAP and CNP are differentiation markers of astrocytes and oligodendrocytes, respectively. An increase in the mRNA level of each marker can be an evidence of the differentiation of neural stem cells into specific cells. In addition, a higher mRNA level of a marker reflects more profound differentiation into the corresponding cells. In the presence of RA, the REP matrix-coated PLGA cell scaffold was found to guarantee the performance of a cytodifferentiation.

Test Example 5

Cell Morphology on Surface of REP Matrix-Coated PLGA Scaffold

Figure 15:
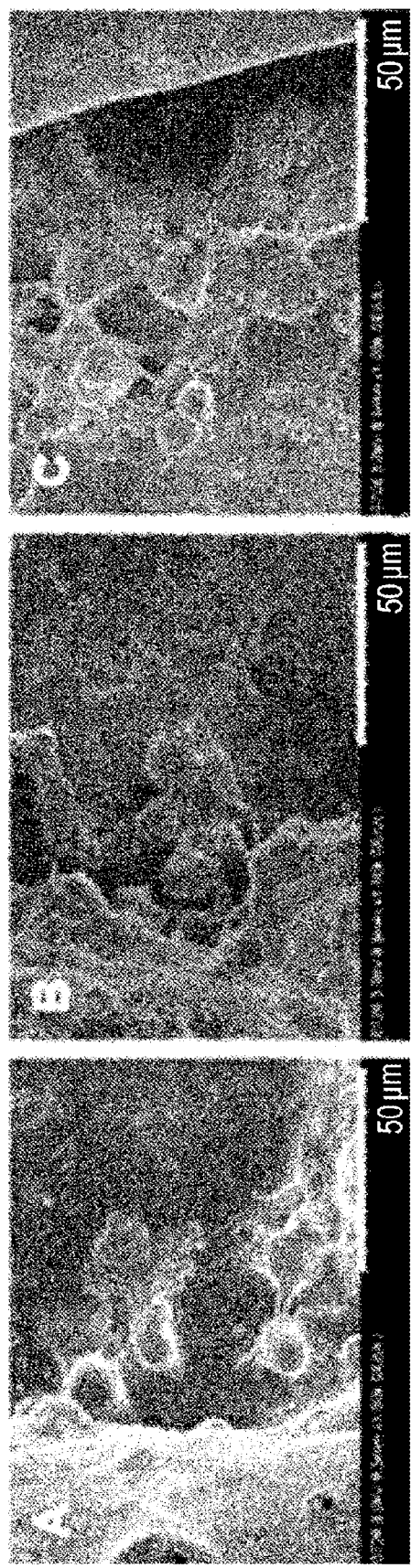
FIG. 15 shows SEM images of NPCs after they were grown for 8 hrs on the PLGA scaffolds in the manner described in Test Example 5 (A: S3, B: S4, C: S5).
Figure 16:
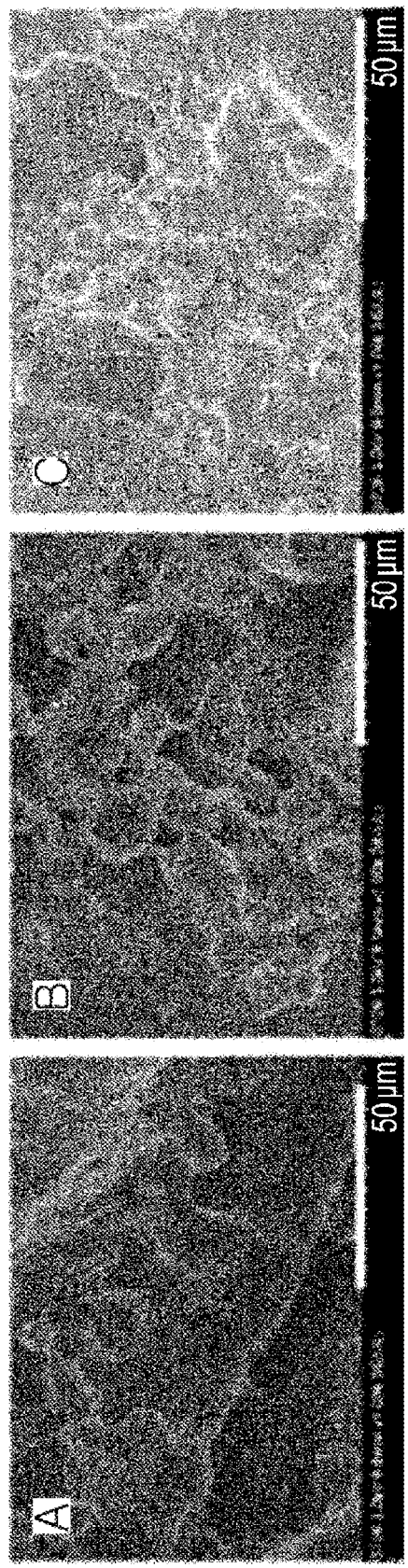
FIG. 16 shows SEM images of NPCs after they were grown for 36 hrs on the PLGA scaffolds in the manner described in Test Example 5 (A: S3, B: S4, C: S5).
Figure 17:
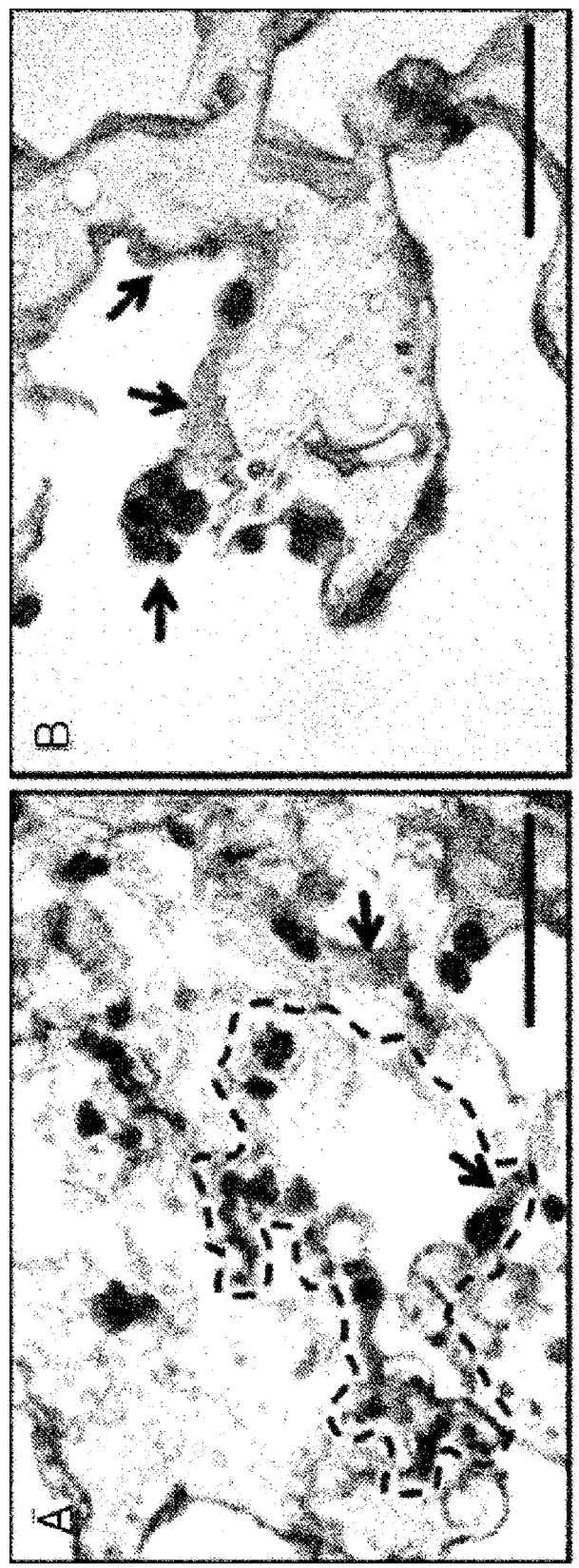
FIG. 17 shows SEM images of NPCs grown on the REP matrix-coated PLGA scaffold after H&E-staining for illustrating cell morphologies in the manner described in Test Example 5 (A: S4, B: S4+RA).

For morphological observation, NPCs were incubated on each of the REP matrix-coated PLGA scaffolds of Example 3 in the same manner as in the cell differentiation assay of Test Example 4. The scaffolds on which the cells were grown were photographed by SEM in the same manner as in Test Example 2-1, and in the same manner as in Test Example 2-2 after H&E staining. SEM images of the former are shown in FIGS. 15 and 16 while SEM images of the latter are given in FIG. 17.

As can be seen in FIGS. 15A to 15C, NPCs were grown in the form of circles with a diameter of 10~20 µm after 8 hrs of incubation on S3, S4 and S5.

FIGS. 16A to 16C indicate that after 36 hours of incubation on S3, S4 and S5, NPCs diffused to the extent that they were connected to each other to form a multicellular layer composed of globular cells.

In FIG. 17A, NPCs that were grown for 8 days on S4 in the absence of retinoic acid had circular morphology, as visualized by H&E-staining. When cultured on S4 in the presence of 10 µM retinoic acid for 8 days, as shown in FIG. 17B, NPCs grew separately or in an agglomerated form within the REP matrix coat.

This resulted from the promoted migration of cells on the REP substrate-coated PLGA cell scaffold. As demonstrated by the cell agglomerates, the REP matrix-coated cell scaffold of the present invention helps cell migration and thus promotes cell proliferation and differentiation through intercellular interaction.

Taken together, the data obtained through Examples and Test Examples demonstrate that the REP matrix-coated PLGA scaffolds of the present invention provide microenvironments suitable for the proliferation and differentiation of cells as well as cell adhesion and migration, thus finding applications as biocompatible materials in stem cell implantation for tissue regeneration.

The invention claimed is:

1. A method for fabricating a cell scaffold, comprising:
dissolving a PLGA (poly(D,L-lactide-co-glycolide)) substrate in an organic solvent to give a PLGA solution; and adding an effervescent agent to the PLGA solution to afford a PLGA scaffold with a porous structure;
coating the PLGA scaffold with an elastin-like artificial extracellular matrix
comprising a compound represented by the following General Formula 1:

TGPG[VGRGD(VGVPG)$_n$]$_m$     [General Formula 1]

wherein, n is an integer meeting 2<n<, and m is an integer meeting 10<m<30.

2. The method of claim 1, wherein the elastin-like artificial extracellular matrix is applied in an amount of 1 to 200 µg per 1 cm$^2$ of a cross sectional area of the PLGA scaffold.

3. The method of claim 1, further comprising treating the elastin-like artificial extracellular matrix-coated scaffold with a cytodifferentiation agent.

4. The method of claim 3, wherein the cytodifferentiation agent comprises retinoic acid.

5. The method of claim 1, wherein the organic solvent comprises at least one selected from the group consisting of tetrahydrofuran, dimethyacetamide, dimethylformamide, chloroform, dimethylsulfoxide, butanol, isopropanol, isobutylalcohol, tetrabutylalcohol, acetic acid, 1,4-dioxane, toluene, ortho-xylene, and dichloromethane.

6. The method of claim 1, wherein the PLGA solution contains the organic solvent in an amount of 4,000~5,000 weight parts based on 100 weight parts of PLGA.

7. The method of claim 1, wherein the PLGA has a molecular weight of 40,000~75,000, with a glycolide content of 80~150 weight parts per 100 weight parts of lactide.

8. The method of claim 1, wherein the PLGA solution further comprises an organic acid.

9. The method of claim 8, wherein the organic acid comprises citric acid.

10. The method of claim 8, wherein the PLGA solution comprises the effervescent agent in an amount of 100~300 weight parts, and the organic acid in an amount of 2~20 weight parts, based on 100 weight parts of PLGA.

11. The method of claim 1, wherein the effervescent agent comprises at least one selected from the group consisting of $NaHCO_3$, $Na_2CO_3$, $KHCO_3$, $K_2CO_3$, $CaCO_3$, and $Li_2CO_3$.

12. A cell scaffold, comprising a PLGA (poly(D,L-lactide-co-glycolide) scaffold; and an elastin-like artificial extracellular matrix comprising a compound represented by the following General Formula 1:

   [General Formula 1]

wherein, n is an integer meeting $2 \leq n \leq$, and m is an integer meeting $10 \leq m \leq 30$.

13. The cell scaffold of claim 12, wherein the PLGA scaffold is coated with the elastin-like artificial extracellular matrix in an amount of 1 to 200 μg per $cm^2$ of a cross sectional area of the PLGA scaffold.

14. The cell scaffold of claim 12, wherein the PLGA has a molecular weight of 40,000~75,000.

15. The cell scaffold of claim 12, wherein the PLGA contains a glycolide content of 80~150 weight parts per 100 weight parts of lactide.

16. The cell scaffold of claim 12, further comprising a cytodifferentiation agent.

17. The cell scaffold of claim 12, wherein the PLGA scaffold has a porous structure, with a porosity of 30~50%, as measured by image analysis of H&E-stained cross-sectional specimens.

* * * * *